(12) United States Patent
Chang et al.

(10) Patent No.: US 8,542,901 B2
(45) Date of Patent: Sep. 24, 2013

(54) METHOD FOR CORRECTING MOTION ARTIFACTS IN MAGNETIC RESONANCE IMAGES

(75) Inventors: Ti-chiun Chang, Princeton Junction, NJ (US); Tong Fang, Morganville, NJ (US); Michelle Xiaohong Yan, Princeton, NJ (US)

(73) Assignee: Siemens Aktiengesellschaft, Münich (DE)

( * ) Notice: Subject to any disclaimer, the term of this patent is extended or adjusted under 35 U.S.C. 154(b) by 960 days.

(21) Appl. No.: 12/632,240

(22) Filed: Dec. 7, 2009

(65) Prior Publication Data

US 2010/0142789 A1    Jun. 10, 2010

Related U.S. Application Data

(60) Provisional application No. 61/120,093, filed on Dec. 5, 2008.

(51) Int. Cl.
*A61B 6/03* (2006.01)
(52) U.S. Cl.
CPC .................................... *A61B 6/03* (2013.01)
USPC ........................................................ 382/131

(58) Field of Classification Search
CPC ........................................................ A61B 6/03
USPC ........................................................ 382/131
See application file for complete search history.

(56) References Cited

PUBLICATIONS

Lin et al., Correcting Bulk In-Plane Motion Artifacts in MRI Using the Point Spread Function, 2005, IEEE Transactions on Medical Imaging, vol. 24, No. 9, pp. 1170-1176.*
Raj et al., A Graph Cut Algorithm for Generalized Image Deconvolution, 2005, Proceedings of the Tenth IEEE International Conference on Computer Vision (ICCV'05), pp. 1-7.*
Lee et al., Compensation of Motion Artifacts in MRI via Graph-Based Optimization, Presented Jun. 20-25, 2009, Proceedings of the IEEE Conference on Computer Vision and Pattern Recognition CVPR2009, pp. 2192-2199.*

* cited by examiner

*Primary Examiner* — Hoon Song
*Assistant Examiner* — John Corbett
(74) *Attorney, Agent, or Firm* — Donald B. Paschburg

(57) ABSTRACT

For resonance image data of an imaged subject, a method that first detects and estimates the dominant motions of k-space data (i.e., the motion vectors) and then constructs a graphical model for each estimated motion vector. The segments of the k-space that are determined to be corrupted by motion are restored by minimizing the energy associated with the corresponding graphical model. Consequently, the MR image of the imaged subject becomes free of motion artifacts.

20 Claims, 4 Drawing Sheets

METHOD FOR CORRECTING MOTION ARTIFACTS IN MAGNETIC RESONANCE IMAGES

CROSS-REFERENCE TO RELATED APPLICATIONS

This application claims the benefit of Provisional U.S. Patent Application Ser. No. 61/120,093 entitled, "Motion Correction In MRI Using Graph-Based Optimization", filed in the name of Ti-chiun Chang, Michelle Xiao-Hong Yan, and Tong Fang on Dec. 5, 2008, the disclosure of which is also hereby incorporated herein by reference.

FIELD OF INVENTION

The present invention relates to magnetic resonance imaging (MRI). More particularly, the present invention relates to MRI that corrects motion artifacts.

BACKGROUND OF THE INVENTION

Magnetic resonance imaging (MRI) is a non-invasive diagnostic imaging procedure that uses nuclear magnetization and radio waves to produce internal images of a patient. Briefly, an MRI scanner contains magnetic coils that create a strong static magnetic field in which the patient is positioned. Certain atoms in a patient's body that were previously randomly-ordered become aligned along the magnetic field. The scanner then sends a series of bursts or pulses of radio frequency (RF) energy through the patient's body part under examination that excite the "ordered" atoms to a specific oscillation around the magnetic field. The atoms give up the RF energy, i.e., generate an RF signal, each time the atoms return to their respective alignments during the oscillation. The scanner detects the RF signals by appropriate reception or pick-up coils and uses gradient coils to generate non-homogeneous magnetic fields to enable the signals to be spatially coded in all three spatial directions. The scanner processes the coded signals or data to transform them into a visual representation of the patient's body part. In particular, the scanner digitizes the signals, creates a so-called k-space matrix (frequency domain data) filled with the digitized complex values of each signal, and generates for display and/or other usage a corresponding MR image from the k-space matrix by means of a complex Fourier transformation. The MRI scanner acquires three-dimensional image data of the patient's body part for respective "slices" of an area of the body part. The scanner repeats a pre-defined MR image pulse sequence, i.e., the above-described steps for collecting the signals/data, a number of times to collect sufficient data from the excitations to reconstruct the specific image. Ideally, there are little or no variations in the nuclear magnetization during the excitations. However, movement by the patient, voluntary or involuntary, may affect the nuclear magnetization and the subsequent MR image reconstruction.

In fact, motion artifacts due to patient motion during the image acquisition are a very common problem in MRI. Motion artifacts, especially those caused by large motions, can significantly degrade the quality of MR images (e.g., ghosting and/or blurring. As described above, in MRI, time signals of an imaged patient or subject are produced by controlling a sequence of RF pulses and time-varying gradient magnetic fields. Matching a time signal to the location of its source generates image data known as spatial encoding. This can be accomplished because variations in the magnetic field cause the time signals to have frequencies that are functions of position. These time signals are acquired during scanning and thereafter mapped into a 2-D array, i.e. the k-space. The time signals are acquired by a line readout along the x-direction in separate scans and the line readout signals are collected row by row to fill the k-space. Normally, the x-direction is referred to as the frequency encoding (FE) direction while the y-direction is referred to as the phase encoding (PE) direction. A reconstruction algorithm, most often the inverse Fourier transform (IFT), is then used to convert the k-space information to an image of the patient or subject. Data acquisition is extremely rapid in the FE direction (msec/degree) so motion can be largely ignored. The time intervals in the PE direction are much longer (sec/degree). Therefore, inconsistencies that exist in k-space due to patient motion (in the form of phase shifts) occur between lines in the PE direction. Motion artifacts in the subject image are a consequence of these phase shifts. Removing motion artifacts is usually then formulated as recovering phase information in the frequency domain.

Many methods and devices have been developed to remove patient or subject motions and restore MR images. Some directly measure motion. For example, navigation-echo is a traditional technique for handling patient or subject motions. Briefly, an echo signal ("navigator" echo) is introduced to pass through the center of the data space i.e., k-space, and phase variations are detected by use of further signal processing and reconstruction algorithms. Computational methods are then used to correct the undesired view-to-view phase variations and eliminate a significant source of motion artifacts in an image. The navigator echo method is more fully described in an article by R. L. Ehman and J. P. Felmlee, "Adaptive technique for high-definition MR imaging of moving structures", *Radiology* vol. 173, no. 1, pp. 255-263, October 1989. However, the navigation-echo technique requires some special pulse sequences which are not available in all commercial scanners or for all applications. In another technique, motion is estimated by attaching external markers to the imaged subject; but this approach may not be practical in all applications. This is more fully described in an article by A. S. Fahmy, B. Tawtik, and Y. M. Kadah, "Robust estimation of planar rigid body motion in magnetic resonance imaging", *Proc. International Conference on Image Processing*, vol. 2, 2000, pp. 487-490 vol. 2.

Another method to address motion artifacts uses techniques to observe the features of images to determine patient motions. This type of method does not require special scanners or special pulse sequences. Instead, this method needs a good metric which can measure the quality of images. Examples are entropy criterion (described in the article by D. Atkinson, D. L. G. Hill, P. N. R. Stoyle, P. E. Summers, and S. F. Keevil, "Automatic correction of motion artifacts in magnetic resonance images using an entropy focus criterion", *IEEE Transactions on Medical Imaging*, vol. 16, no. 6, pp. 903-910, 1997 and the article by D. Atkinson, D. L. Hill, P. N. Stoyle, P. E. Summers, S. Clare, R. Bowtell, and S. F. Keevil, "Automatic compensation of motion artifacts in MRI", *Magnetic Resonance in Medicine*, vol. 41, no. 1, pp. 163-170, January 1999) and normalized gradient squared (NGS) (described in the article by A. Manduca, K. P. McGee, E. B. Welch, J. P. Felmlee, R. C. Grimm, and R. L. Ehman, "Autocorrection in MR imaging: adaptive motion correction without navigator echoes", *Radiology*, vol. 215, no. 3, pp. 904-909, June 2000). Some image metric-based techniques have been employed in clinical settings and their results are comparable with the navigator-echo techniques. An evaluation of various metrics is described in an article by K. P. Mcgee, A. Manduca, J. P. Felmlee, S. J. Riederer, and R. L. Ehman, "Image metric-based correction (autocorrection) of motion effects: Analysis of image metrics", *Journal of Magnetic Resonance Imaging*, vol. 11, no. 2, pp. 174-181, 2000. These metrics are mainly global image metrics which are applied to the whole image to compute a single score.

An important issue in the image metric-based method is the optimization procedure, i.e., how to minimize the image metric. In one technique, the rows of MR signals data (k-space) are grouped into several intervals. For each interval, the motions (dx, dy) in $\{-m \cdot s, -(m-1) \cdot s, \ldots, m \cdot s\} \times \{-m \cdot s, -(m-1) \cdot s, \ldots, m \cdot s\}$ are evaluated with an image metric. Then, the motion with the best image quality measure is selected as the motion associated with the segment and is also applied to compensate the motion artifact at this segment. The efficiency of the algorithm depends on the size of the so-called metric map. This is described more fully in the first article noted above by D. Atkinson, et al. In another technique, a systematic approach, called center-out, is used to find the motion and compensate for the motion artifact sequentially from the center to outer segments. This is described more fully in the second article noted above by D. Atkinson, et al. Another optimization technique replaces the normalized gradient squared (NGS) measure by the entropy measure to find a pattern in the NGS metric map that can be used to reduce the evaluations in NGS. However, this technique is too rough and simply using the mentioned metrics may easily fail to correct the MR images with motion artifacts due to large motions. More recently, a more sophisticated image metric-based method, called EXTRACT, has been described that is based on extrapolation of the k-space data and the metric is the correlation value between extrapolated k-space data and a tested k-space data. This is described more fully in an article by W. Lin, and H. K. Song, "Extrapolation and correlation (EXTRACT): a new method for motion compensation in MRI", *IEEE Transactions on Medical Imaging*, vol. 28, Issue 1, January 2009, pp 82-93.

The image metric-based methods generate a set of trial motions for each PE scan and the best motion is selected after evaluating the values of image metrics for all trial motions. Several techniques have been applied to minimize the image metrics and they perform well for small motions. Generally, however, due to high dimensionality of the search space and the complicated image metrics, the correct minimizer is hard to locate when the original MR signals are corrupted by large motions.

The MRI motion artifact compensation problem is similar to the blind image restoration problem where the goal is to estimate the corruption-free image and the blur (i.e., motion point spread function (PSF)) kernel from the MR image with motion artifacts with the motion PSF being unknown. According to convolution theorem, the IFT of the observed k-space data is the convolution of the IFT of the corruption-free k-space data and a kernel which is the IFT of the phase shift as mentioned above. Although this problem formulation is similar to blind image restoration, state-of-the-art de-blurring or deconvolution methods can not be applied because this kernel is a complex matrix and its size is as large as the size of the k-space data, i.e., the image size. In addition, the kernel for MRI motion artifacts has a specific form.

SUMMARY OF THE INVENTION

The above problems are obviated by the present invention which provides a method that obtains magnetic resonance image data from an imaged subject, estimates the dominant motion in the image data, constructs a graphical model for the estimated dominant motion, and optimizes the graphical model so that the image data corrupted by the motion of the imaged subject is corrected. The image data may be k-space data for the imaged subject. In such case, the estimating step may be estimating the motion vectors in the k-space data and the constructing step may be constructing a graphical model for each estimated motion vector. The optimizing step may comprise minimizing the energy associated with the graphical models to obtain the motion vectors corrupted by the motion of the subject and compensating for the corrupted motion vectors. The minimizing and compensating steps are then repeated until no corrupted motion vectors are obtained. The minimizing step may be applying the iterated conditional modes algorithm to the graphical models to determine the motion vectors corrupted by the motion of the subject.

Alternatively, the present invention provides a method that obtains magnetic resonance image data of an imaged subject that contains motion artifacts and transforms the magnetic resonance image data into k-space data. The method then determines motion vectors in the k-space data likely causing motion artifacts; constructs a graphical model for each motion vector, and determines, from the graphical models, the motion vectors that are causing motion artifacts. The method then compensates for the motion vectors that are causing motion artifacts to produce a magnetic resonance image of a subject with compensated motion artifacts.

Determining the motion vectors may comprise constructing a gradient magnitude map of the k-space data and estimating the motion vectors from the gradient magnitude map. Constructing a gradient magnitude map may further include constructing a low gradient magnitude map. Estimating the motion vectors may further include applying a normalized cross correlation algorithm for the low gradient magnitude map to determine motion vectors in the k-space data likely causing motion artifacts. Also, constructing a low gradient magnitude map may comprise constructing a gradient magnitude map of the k-space data; locating edge fragments in the k-space with high gradient magnitudes; and re-constructing the gradient magnitude map without edge fragments with high gradient magnitudes.

Further, constructing a graphical model may include constructing each graphical model with the normalized gradient squared as the image quality metric. Further, determining, from the graphical models, motion vectors that are causing motion artifacts may comprise applying the iterated conditional modes algorithm to the graphical models to determine these motion vectors. Further, compensating for motion vectors that are causing motion artifacts may comprise applying to the k-space data inverse motion vectors for these motion vectors. Still further, the steps of determining, from the graphical models, motion vectors that are causing motion artifacts and compensating for them may be repeated until no further motion vectors that are causing motion artifacts are determined.

Alternatively, the present invention provides a magnetic resonance imaging apparatus that comprises means for obtaining magnetic resonance image data of an imaged subject that contains motion artifacts and means for transforming the magnetic resonance image data into k-space data. The apparatus also comprises means for estimating the dominant motion in the k-space data; means for constructing a graphical model for the estimated dominant motion; and means for optimizing the graphical model so that the k-space data containing the motion artifacts is corrected.

The present invention provides a novel approach to resolve the MRI motion correction problem. The present invention takes advantage of the special structure of the motion PSF kernel for the MRI motion artifacts. The present invention provides a method that detects dominant motions from the corrupted patient image and formulates the MRI motion estimation problem as a graph-based optimization problem in order to estimate the motion for each segment in the k-space data. Specifically, the magnitude of the blur PSF, or motion PSF, for the MRI motion artifact may contain many peaks, each peak corresponding to a motion vector. A large peak in the magnitude map may represent a new or artificial image structure due to a ringing effect by a strong image structure. Hence, the inventive method first locates strong edges in the k-space data and similar image structures (i.e., ringing counterparts) from the image to estimate the locations of peaks in the PSF kernel. For each estimated motion vector, a binary variable is associated with a segment in k-space to denote if it is corrupted by this motion or not. The method combines all these binary variables in a graph and formulates the motion estimation problem as a graph-based optimization problem, which is solved by minimizing the energy associated with the graph. Experimental results show that a method in accordance with the present invention provides satisfactory compensation of motion artifacts in an MR image even when large motions of the patient or subject are involved.

In short, previous methods for compensating for motion artifacts are mainly image metric-based, and they may easily fail when the motion is large because they do not consider the structure of the motion kernal. State-of-the-art blind restoration algorithms can not be applied in such cases either because they cannot handle a complex kernel that is as large as the size of the image. The present invention provides a novel approach utilizing the image structure to decompose, or segment, the kernel into several fragments. Based on this kernel representation, determining a kernel fragment is formulated as a binary optimization problem, where each binary variable represents whether a segment in MR signals (k-space) is corrupted by a certain motion or not. The relationship between variables is established graphically and the kernel is estimated by minimizing the energy associated with the graphical models.

DESCRIPTION OF THE DRAWINGS

For a better understanding of the present invention, reference is made to the following description of an exemplary embodiment thereof, and to the accompanying drawings, wherein.

DETAILED DESCRIPTION

Figure 1:
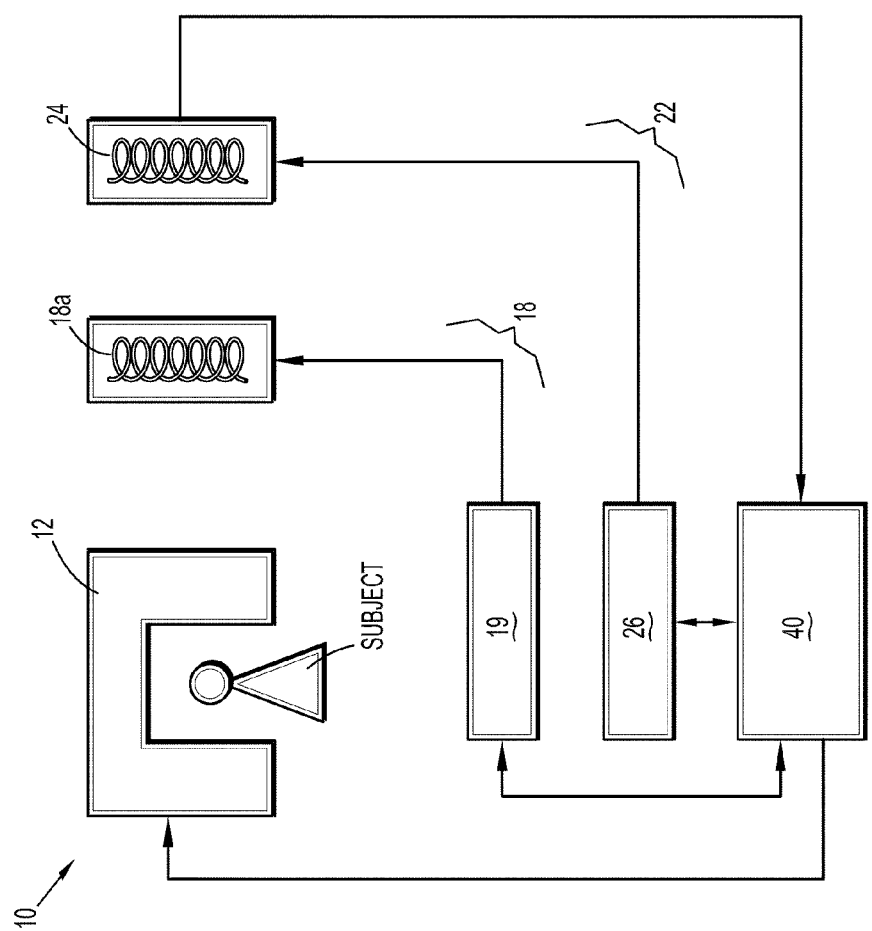
FIG. 1 is a block diagram of an MR scanner operable in accordance with the present invention.

FIG. 1 is a block diagram of an MRI scanner 10 that corrects MRI motion artifacts operable in accordance with the present invention. A main magnet 12 generates a strong static magnetic field in an imaging region where the patient or the specific body part of the patient to be examined is introduced. The magnet 12 is used to polarize the patient's body part, i.e., certain atoms in the patient's body part that were previously randomly-ordered become aligned along the magnetic field. A gradient coil system 18, having a gradient coil 18a and a gradient coil control unit 19, generates a time-varying linear gradient field in respective spatial directions, x, y and z, and spatially encodes the positions of the polarized or excited atoms. An RF system 22, having an RF antenna 24 and a pulse generation unit 26, transmits a series of RF pulses to the patient's body part to excite the "ordered" atoms of the patient's body part. A control or computer system 40 coordinates the pulse generation unit 26 and the gradient coil control unit 19 to carry out a desired MR image pulse sequence. The scanner 10 repeats the MR image pulse sequence a number of times so the atoms oscillate between a polarized state of alignment with the main magnetic field and an excited state caused by the energy of RF pulses. The atoms release the RF energy, i.e., generate an RF signal, each time the atoms return to their respective alignments during the resonance or oscillation. The RF system 22 detects the released RF energy and generates spatially-coded MR signals to the computer system 40.

Figure 2:
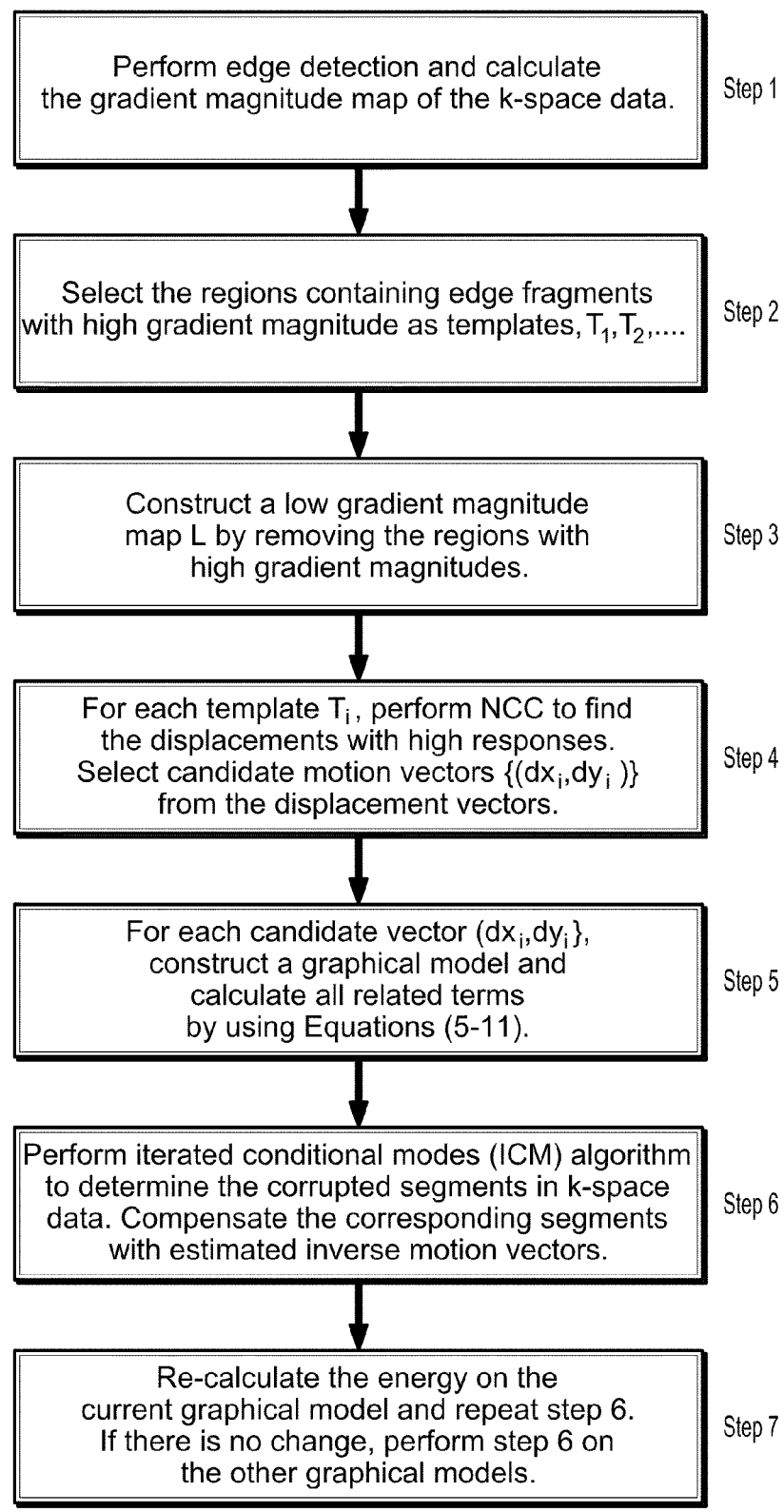
FIG. 2 is a flow chart of the steps of a method of operation by the MR scanner of FIG. 1 in accordance with the present invention.

The computer system 40, which controls the operation of the MR scanner 10 and its components, processes the MR signals to transform them into a visual representation of the patient's body part (i.e., reconstructed MR images). In particular, the computer system 40 digitizes the signals, constructs a k-space matrix filled with the digitized complex values of each signal, and generates for display, storage, and/or other usage a corresponding MR image from the k-space matrix using well-known mathematical techniques, such as a complex Fourier transformation. Movements by the patient in the imaging region are likely to affect the nuclear magnetization and image reconstruction. To compensate for these motion artifacts in the MR images, the computer system 40 is adapted to operate the MR scanner 10 according to a method of the present invention as shown in FIG. 2.

The following describes the formulation for the MRI motion correction problem. An important property of k-space data is that it exhibits Hermitian symmetry, which means it is equal to its own conjugate transpose. To be more specific, for a matrix F containing data in k-space, we have $F=F^H$, where the superscript H indicates the conjugate transpose operation. This is true if and only if the image is real due to the MR techniques and spin signals. However, the real k-space data is complex because of noises and artifacts.

The motion corruption process in the spatial domain is now detailed. Assume a rigid motion (dx,dy) occurs in scanning the n number of scans. The original k-space data F is multiplied by a mask of phase shift in an element-wise manner. The corrupted k-space G can be written in the following form:

$$G(k_x,k_y)=F(k_x,k_y) \circ M_{dx,dy}^n(k_x,k_y), \qquad (1)$$

where $\circ$ is the point-wise matrix multiplication and $M^n_{dx,dy}$ is the transfer function due to the motion (dx,dy) at the n-th segment of the k-space data given by:

$$M_{dx,dy}^n(k_x,k_y)=rect(k_{y-n})\exp(-j2\pi(dx \cdot k_x+dy \cdot k_y)) \qquad (2)$$

where $k_x$ is frequency-encoding line and $k_y$ is phase-encoding line, rect(t) is the 1-D rectangular function which is 1 when $|t|<0.5$.

A corrupted k-space can include several corrupted scans. If we consider the spatial domain, the motion PSF kernel k can be derived from Equation 1 as follows:

$$FT^{-1}\{G\}=FT^{-1}\{F\} \otimes FT^{-1}\Sigma_i M_{dx_i dy_i}^{n_i}, \qquad (3)$$

where $FT^{-1}$ is the inverse Fourier transform (IFT) and $\otimes$ is the 2-D convolution. Thus, we can write the motion PSF kernel as:

$$k=FT^{-1}\{\Sigma_{i_1} M_{dx_1 dy_1}^{n_1}\} \text{ and}$$

$$k \propto \Sigma_i[\delta(x-dx_i,y-dy_i)] \otimes [\exp^{-j2\pi M}\text{sinc}(y)\delta(x-dx_i)]. \qquad (4)$$

Figure 3A:
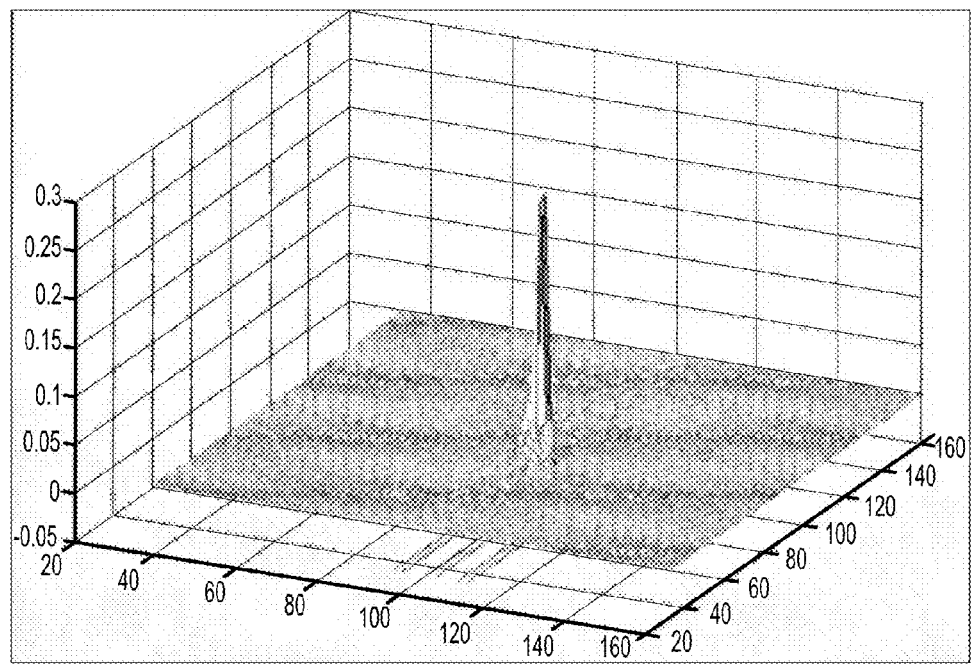
FIGS. 3a, 3b show the magnitude maps of two exemplary motion PSF kernels for MRI motion artifacts.
Figure 3B:
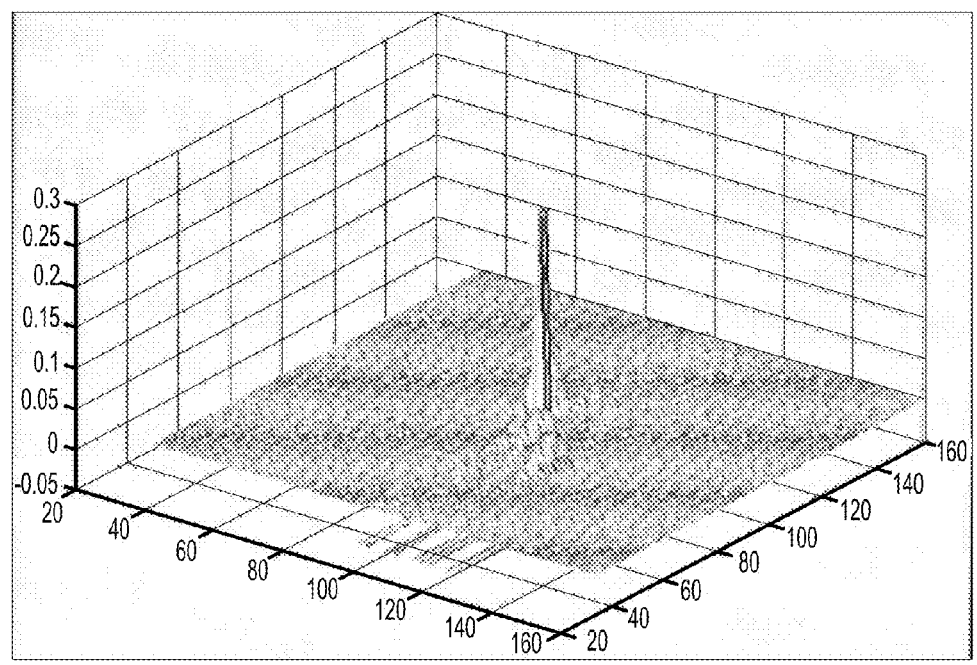

By observing the motion PSF kernel k, we can see that the kernel is composed of several motions, denoted by $(dx_i, dy_i)$. Each motion $(dx, dy)$ corresponds to a line vertical to the y-axis, and a peak in the magnitude appears at the location $(dx, dy)$. FIG. 3 shows the magnitude map of two exemplary motion PSF kernels for MRI motion artifacts. FIG. 3a shows a kernel with a single motion vector and FIG. 3b shows a kernel with two different motion vectors. They are calculated by IFFT. The center is $(dx, dy)=(0, 0)$.

Ideally, the k-space data has the conjugate symmetry property, so that the 1 FT of f is a real image. However, as noted above, the images mentioned here are complex. If the motion $(dx, dy)$ is only involved in the motion PSF kernel, the two peaks are shown in the magnitude of the kernel. The first one is the origin, and the other is the point $(dx, dy)$. Without loss of generality, the simplest unit step function $u(.)$ is served as the original image $I(x, y)$, and it is given by $u(x-y)$. In the corrupted image, the line L: $(y-dy)=(x-dx)$ will have a value that is the integral of $[\exp(-j2\pi\, n_i)\mathrm{sinc}(y)]$ over y, and this integral value is very different from the surrounding background for most $n_i$. Therefore, the original image structure may be recurrent in the spectrum of the corrupted image, and the location difference between two similar structures provides a good estimation of the motion vectors involved in the motion artifact of an MR image. Because most segments are not corrupted, the peak in the origin has the largest value of any other peaks in the spectrum. In addition, the strong structure can still be detected from the motion corrupted image.

The present invention provides a scanner 10 and method of operation to correct the motion corrupted image as shown in FIG. 2. Generally, the method first detects and estimates the dominant motions of the k-space data (i.e., the motion vectors) and then constructs a graphical model for each estimated motion vector. The segments of the k-space that are corrupted by motion are restored by minimizing the energy associated with the corresponding graphical model. Consequently, the MR image of the imaged patient becomes free of motion artifacts. The details of a method of operation for the MR scanner 10 in accordance with the present invention are described below. As part of the estimation of motion vectors, the method first performs edge detection to preserve object boundary structures. A technique for edge detection is described more fully in an article by J. Canny, "Computational approach to edge detection", *IEEE Trans. Pattern Analysis and Machine Intelligence,* 8:679-714, 1986. The method then calculates a gradient magnitude map of the k-space data. The edge fragments with high gradient magnitude are regarded as strong structures, and the strong structures accompanied with their neighboring pixels are collected to form a set of templates. These templates are not necessarily rectangular, and they may be arbitrarily-shaped S. The method then performs normalized cross correlation (NCC) described in Equation 5 on a low gradient magnitude map which is the gradient magnitude map with strong structures removed. After performing template matching with arbitrarily-shaped NCC, the vectors from the template center to the locations with high response are candidates for motion vectors, $$NCC(x, y) = \frac{\sum_{i,j \in S}(T(i,j) - \overline{T})(I(x+i, y+j) - \overline{I})}{\sqrt{\sum_{i,j \in S}(T(i,j) - \overline{T})^2}\sqrt{\sum_{i,j \in S}(I(x+i, x+j) - \overline{I})^2}}, \quad (5)$$

where T is the mean of the template in the shape S and I is the mean of the image in the shape S with center $(x, y)$.

To collect these template matching results from different templates, a voting array containing all motion vectors is used to collect responses from different NCC matching.

The method then constructs and optimizes a graphical model. For each candidate motion vector $(dx, dy)$, the method determines whether the segment is corrupted or not. The method makes use of the image quality metric and the conjugate symmetric property for the motion-free k-space data to create a graphical model. The method uses the normalized gradient squared (NGS) as the image quality metric although others may also be used. A greater NGS value means a better quality of image and the formula is in the following equation:

$$NGS(I) = \frac{\sum_{x,y}\|\nabla I\|^2}{\left(\sum_{x,y}\|\nabla I\|\right)^2}. \quad (6)$$

Figure 4:
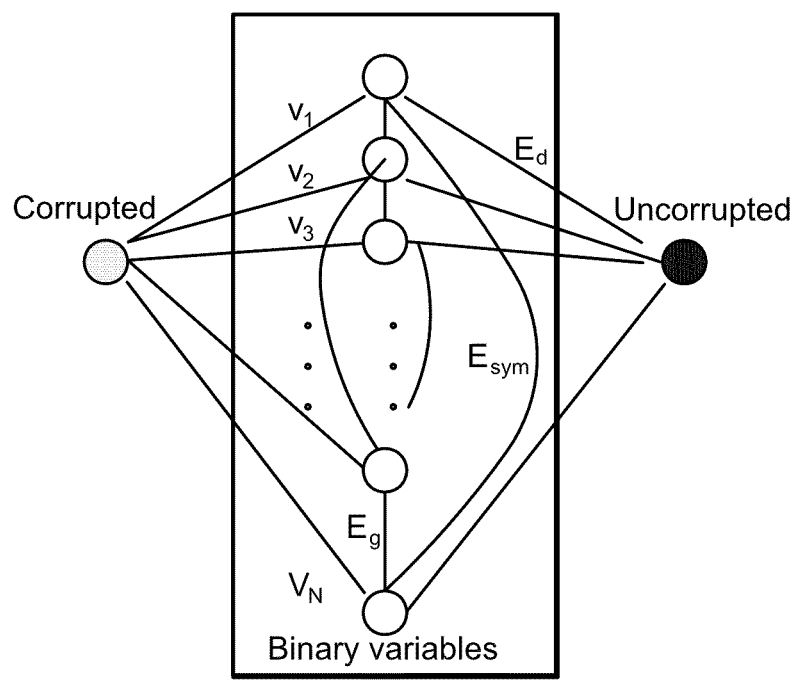
FIG. 4 is a schematic representation of a graphical model of a dominant motion vector of the method of FIG. 2 in accordance with the present invention.

An exemplary graphical model for determining which segments contain corruption due to a dominant motion is shown in FIG. 4. Here, the number of binary nodes is the same as the number of phase-encoding lines, N, in the k-space data. The i-th binary variable $V_i$ represents if the scan I is corrupted or not. Hence, the problem is transformed into a labeling problem. The energy E for this labeling problem is composed of three terms, i.e., $E_d(.)$, $E_g(.,.)$, and $E_{sym}(.,.)$, with a weighting parameter $\alpha$, $$E = \Sigma_i E_d(V_i) + \Sigma_{|i-j|=1} E_g(V_i) + \alpha \Sigma_{|i-j|=2N} E_{sym}(V_i). \quad (7)$$

Note that $E_d(V_i)$ is similar as the common data term in the graphical model; $E_g(V_i, V_j)$ and $E_{sym}(V_i, V_j)$ are similar to the smoothness terms. The term $E_d(V_i)$ is defined as the NGS image metric which is computed with motion compensation if $V_i=1$. $E_d(V_i=0)$ is defined as the NGS value of the current image (corrupted image), and $E_d(V_i=1)$ is the NGS value of the image when the motion $(-dx, -dy)$ is corrected at the i-th row, $$E_d(V_i=0) := -NGS(|FT^{-1}\{G(k_x,k_y)\}|), \quad (8)$$

$$E_d(V_i=1) := -NGS(|FT^{-1}\{FoM_{-dx,-dy}^i\}|). \quad (9)$$

The term $E_g(V_i, V_j)$ can be regarded as the gain if two adjacent PE line scans are motion-compensated at the same time. $E_d(V_i=1)$ and $E_d(V_j=1)$ are the NGS values of the k-space data with the motion $(-dx, -dy)$ corrected at the i-th and j-th rows, respectively. These rows are considered as individual compensation. The adjacent rows usually have similar phase-encoding; hence, the method tries to consider the adjacent rows at the same time. First, the method compensates these two rows. Then, the gain can be calculated as follows. If both of these two rows should be compensated, $E_g(V_i=1, V_j=1)$ will be negative, $$E_g(V_i=1, V_j=1) := -NGS(|FT^{-1}\{GoM_{-dx,-dy}^i\, oM_{-dx,-dy}^j\}|) - E_d(V_i=1) - E_d(V_j=1). \quad (10)$$

If two adjacent rows have different labels, the method simply uses a constant to penalize, $$E_g(V_i=0, V_j=1) := \beta$$

$$E_g(V_i=1, V_j=0) := \beta$$

$$E_g(V_i=0, V_j=0) := 0$$

The term $E_{sym}(V_i,V_j)$ is a measure of conjugate symmetry of k-space data given the label of i-th PE line scan and j-th PE line scan. If $V_i$=1 or $V_j$=1, it means that the motion (−dx, −dy) is applied to the corresponding row. Then, the magnitude D of the difference of the k-space data and its Hermitian transpose is calculated. $E_{sym}(V_i, V_j)$ is defined by the Frobenius norm of this matrix D. The detailed equations are listed in Equation (11):

$$E_{sym}(V_i=1,V_j=1):=\|abs(GoM_{-dx,-dy}{}^i - (GoM_{-dx,-dy}{}^j)^H)\|_F^2$$

$$E_{sym}(V_i=1,V_j=0):=\|abs(GoM_{-dx,-dy}{}^i G^H)\|_F^2$$

$$E_{sym}(V_i=1,V_j=0):=\|abs(G-(GoM_{-dx,-dy}{}^j)^H)\|_F^2$$

$$E_{sym}(V_i=0,V_j=0):=\|abs(G-G^H)\|_F^2 \quad (11)$$

After constructing the graphical model, the method applies the iterated conditional modes (ICM) algorithm to cut the edges of the graph. The algorithm is more fully described in an article by J. Besag, "On the statistical analysis of dirty pictures", *Journal of the Royal Statistical Society, Series 8*, vol. 48, no. 3, pp. 259-302, 1986. For the nodes classified as corrupted, the inverse motions are applied to the k-space data. The parameters of the graph are updated and all variables are classified again until no variables are labeled corrupted.

The overall method of operation for the MR scanner 10 in accordance with the present invention is summarized by FIG. 2 and as follows:

1. Perform edge detection and calculate the gradient magnitude map of the k-space data.
2. Select the regions containing edge fragments with high gradient magnitude as templates, $T_1, T_2, \ldots$.
3. Construct a low gradient magnitude map L by removing the regions with high gradient magnitudes. For example, a threshold above which gradients are removed can be used.
4. For each template $T_i$, perform NCC to find the displacements with high responses. Select candidate motion vectors $\{(dx_i, dy_i)\}$ from the displacement vectors.
5. For each candidate vector $(dx_i, dy_i)$, construct a graphical model and calculate all related terms by using Equations (5-11).
6. Perform iterated conditional modes (ICM) algorithm to determine the corrupted segments in k-space data. Compensate the corresponding segments with estimated inverse motion vectors.
7. Re-calculate the energy on the current graphical model and repeat step 6. If there is no change, perform step 6 on the other graphical models.

To evaluate the method provided by the present invention, experiments were conducted whereby several sets of data were collected. The first dataset is k-space data of an imaged subject obtained from a MR scanner (MR) constructed and operable according to the present invention. Another dataset used is the famous Shepp and Logan head phantom (SL) data which is broadly used in testing novel methods in MRI. Brain MR images to generate k-space data for testing were also used. The experiments simulated motion corrupted data by using several large motions on the k-space data. Each dataset contains several large motions.

The experiments compared the method of the present invention with two image-metric based methods. In the first, its metric is the NGS, and BFGS method with a cubic line search was used as the optimization procedure because the size of the metric map is hard to decide and it performs well in most situations. In the second, EXTRACT is used. The BCGS method is more fully described in articles by C. G. Broyden, "The convergence of a class of double-rank minimization algorithms", *Journal Inst. Math. Applic.*, vol. 6, pp. 76-90, 1970; R. Fletcher, "A new approach to variable metric algorithms", *Computer Journal*, vol. 13, pp. 317-322, 1970; D. Goldfarb, "A family of variable metric updates derived by variational means", *Mathematics of Computing*, vol. 24, pp. 23-26, 1970; and D. F. Shanno, "Conditioning of Quasi-Newton methods for function minimization", *Mathematics of Computing*, vol. 24, pp. 647-656, 1970.

There are some difficult cases in the experiments in which no method provides satisfactory results. If true motions are not integer-valued motion, in most cases, the method of the present invention can find the closest integer motion vectors to compensate the motion artifacts.

For quantitative analysis, the experiments calculated the NGS values of all results. The NGS has been used for assessing the quality of the corrected MR images. The comparisons are shown in Table 1. The average NGS gain of the inventive method is 28.85%, which is better than −24.73% by using EXTRACT, and 14.55'% by using min-NGS method. Table 2 shows similar comparisons on the corrected brain MR images.

TABLE 1

The NGS gain on SL

| Dataset | Corrupted data | Inventive method | min-NGS | EXTRACT |
|---|---|---|---|---|
| SL1 | 2.2370e−4 | 3.1295e−4 | 3.1764e−4 | 1.7995e−4 |
| SL2 | 1.7733e−4 | 1.7782e−4 | 1.7914e−4 | 1.2861e−4 |
| SL3 | 1.7715e−4 | 2.5929e−4 | 1.7830e−4 | 1.2902e−4 |
| Mean gain | 0% | 28.85% | 14.55% | −24.73% |

TABLE 2

The NGS gain on MR and Brain MR

| Dataset | Corrupted data | Inventive method | minNGS |
|---|---|---|---|
| MR1 | 8.9624e−5 | 1.1338e−4 | 1.1996e−4 |
| MR2 | 1.1748e−4 | 1.2571e−4 | 1.2557e−4 |
| MR3 | 1.1941e−4 | 1.5839e−4 | 1.2831e−4 |
| Brain1 | 9.4636e−5 | 1.0805e−4 | 1.0115e−4 |
| Brain2 | 1.0613e−4 | 1.949e−4 | 1.0001e−4 |
| Brain3 | 1.0371e−4 | 1.0667e−4 | 1.0488e−4 |
| Brain4 | 1.0401e−4 | 1.1224e−4 | 1.0522e−4 |
| Mean gain | 0% | 14.81% | 7.37% |

The previous image-metric based methods to correct motion artifacts in MR images are based on minimizing an image metric in the motion space. The present invention minimizes the associated energy in a graphical model by solving the labeling problem. Image-metric based methods are applied to the image, which is the magnitude of 1 FT of the k-space data. They do not exploit the strong inter-relationships of the motion vectors at different segments in k-space data domain. In contrast, the present invention provides an inventive method which is a graph-based optimization approach that takes these relationships into account, thus leading to more reliable motion artifact compensation results. The experimental results showed the present invention performs well in most cases even when large motions are involved in the motion artifact.

Other modifications are possible within the scope of the invention. For example, the subject to be scanned may be an animal subject or any other suitable object rather than a human patient.

Also, the MR scanner 10 may be constructed in various well-known manners and using various well-known components. For example, the computer system 40 may incorporate the control portions of the various scanner 10 components or may be modularly constructed with separate but coordinated units, such as an image processing unit, user interface, MR image pulse sequence control unit, etc. The MR scanner 10 may further comprise multi-element phased array coils which are capable of acquiring multiple channels of data in parallel. In such case, the scanner 10 is adapted to use "parallel imaging" techniques that allow for accelerated imaging.

Most importantly, instead of simply utilizing the inter-relationship between k-space segments via a graphical model for each dominant motion, the present invention may provide a method that combines the graphical models for different motion vectors into a whole graphical model in order to better describe the inter-relationships between different motion vectors.

What is claimed is:

1. A method for compensating for motion by a subject in a magnetic resonance image, comprising:
    a. obtaining magnetic resonance image data from the imaged subject:
    b. estimating the dominant motion in the image data;
    c. constructing a graphical model for the estimated dominant motion; and
    d. optimizing the graphical model so that the image data corrupted by the motion of the imaged subject is corrected.

2. The method of claim 1, wherein the image data is k-space data.

3. The method of claim 2, wherein the estimating step comprises estimating the motion vectors in the k-space data.

4. The method of claim 3, wherein the constructing step comprises constructing a graphical model for each estimated motion vector.

5. The method of claim 4, wherein the optimizing step comprises a) minimizing the energy associated with the graphical models to obtain the motion vectors corrupted by the motion of the subject and b) compensating for the corrupted motion vectors, said minimizing and compensating steps being repeated until no corrupted motion vectors are obtained.

6. The method of claim 5, wherein the minimizing step comprises applying the iterated conditional modes algorithm to the graphical models to determine the motion vectors corrupted by the motion of the subject.

7. A method of producing a magnetic resonance image of a subject with compensated motion artifacts, comprising:
    a. obtaining magnetic resonance image data of the imaged subject, said image data containing motion artifacts;
    b. transforming the magnetic resonance image data into k-space data;
    c. determining motion vectors in the k-space data likely causing motion artifacts;
    d. constructing a graphical model for each motion vector;
    e. determining, from the graphical models, the motion vectors that are causing motion artifacts; and
    f. compensating for the motion vectors that are causing motion artifacts.

8. The method of claim 7, wherein step c) comprises:
    a. constructing a gradient magnitude map of the k-space data; and
    b. estimating the motion vectors from the gradient magnitude map.

9. The method of claim 8, wherein the constructing a gradient magnitude map step comprises constructing a low gradient magnitude map.

10. The method of claim 9, wherein the constructing a low gradient magnitude map comprises constructing a gradient magnitude map of the k-space data; locating edge fragments in the k-space with high gradient magnitudes; and re-constructing the gradient magnitude map without edge fragments with high gradient magnitudes.

11. The method of claim 10, wherein the estimating step comprises applying a normalized cross correlation algorithm for the low gradient magnitude map to determine motion vectors in the k-space data likely causing motion artifacts.

12. The method of claim 9, wherein the estimating step comprises applying a normalized cross correlation algorithm for the low gradient magnitude map to determine motion vectors in the k-space data likely causing motion artifacts.

13. The method of claim 12, wherein step d) comprises constructing each graphical model with the normalized gradient squared as the image quality metric.

14. The method of claim 13, wherein step e) comprises applying the iterated conditional modes algorithm to the graphical models to determine the motion vectors that are causing motion artifacts.

15. The method of claim 14, wherein the compensating step comprises applying to the k-space data inverse motion vectors for the motion vectors that are causing motion artifacts.

16. The method of claim 7, wherein step d) comprises constructing each graphical model with the normalized gradient squared as the image quality metric.

17. The method of claim 7, wherein step e) comprises applying the iterated conditional modes algorithm to the graphical models to determine the motion vectors that are causing motion artifacts.

18. The method of claim 7, wherein the compensating step comprises applying to the k-space data inverse motion vectors for the motion vectors that are causing motion artifacts.

19. The method of claim 7, further comprising repeating steps e) and f) until no further motion vectors that are causing motion artifacts are determined.

20. A magnetic resonance imaging apparatus, comprising:
    a. means for obtaining magnetic resonance image data of an imaged subject, said image data containing motion artifacts;
    b. means for transforming the magnetic resonance image data into k-space data;
    c. means for estimating the dominant motion in the k-space data;
    d. means for constructing a graphical model for the estimated dominant motion; and
    e. means for optimizing the graphical model so that the k-space data containing the motion artifacts is corrected.

* * * * *